United States Patent [19]

Onda et al.

[11] Patent Number: 4,990,690

[45] Date of Patent: Feb. 5, 1991

[54] PROCESS FOR PREPARING AROMATIC POLYHYDRIC ALCOHOL

[75] Inventors: Yuji Onda; Fumisada Kosuge; Masaru Tunoda, all of Niigata, Japan

[73] Assignee: Mitsubishi Gas Chemical Company, Inc., Tokyo, Japan

[21] Appl. No.: 350,395

[22] Filed: May 11, 1989

[30] Foreign Application Priority Data

May 20, 1988 [JP] Japan .................................. 63-122051

[51] Int. Cl.$^5$ ...................... C07C 27/04; C07C 29/132
[52] U.S. Cl. ...................................... 568/814; 568/811
[58] Field of Search ............... 568/811, 814, 844, 852, 568/861, 864

[56] References Cited

U.S. PATENT DOCUMENTS 2,091,800  8/1937  Adkin et al. ........................ 568/814
3,213,145 10/1965  Field ................................... 568/814

FOREIGN PATENT DOCUMENTS 47-35419  9/1972  Japan .................................. 568/814
49-31435  8/1974  Japan .................................. 568/814
1254927   3/1969  United Kingdom ................. 568/814

OTHER PUBLICATIONS

Organic Reaction, vol. VIII, pp. 1–27, John Wiley & Sons, New York (1954).

Primary Examiner—Werren B. Lone
Attorney, Agent, or Firm—Melvin I. Stoltz

[57] ABSTRACT

An industrially meritorious process for preparing aromatic polyhydric alcohol is disclosed. The process can give an extremely high conversion rate of raw material, i.e., aromatic carboxylic acid ester, and an extremely high selectivity to the objective compound. The process comprises catalytic hydrocracking of an aromatic carboxylic acid ester in which an improvement resides in the fact that an ester represented by the general formula $Ar(COOR)_{m'}(CH_2OH)_{n'}$, (wherein Ar means an aromatic group, R is independently selected from normal and branched alkyl groups having at least 6 carbon atoms, m' means an integer of at least 1, n' means zero or a positive integer and m'+n' satisifies the relationship $m'+n' \geq 2$) is used as raw material. An aromatic polyhydric alcohol is a very useful material, especially as a raw material for the preparation of polymeric substances having high heat resistance.

16 Claims, No Drawings

4,990,690

PROCESS FOR PREPARING AROMATIC POLYHYDRIC ALCOHOL

BACKGROUND OF THE INVENTION

1. Field of the Invention

The present invention relates to a process for preparing an aromatic polyhydric alcohol, and, in particular to a process for preparing an aromatic polyhydric alcohol by the catalytic hydrocracking of an aromatic polycarboxylic acid ester.

Aromatic polyhydric alcohols are useful as plasticizers, solvents for paint and varnishes, and raw materials for the production of pharmaceuticals and agricultural chemicals. In addition, they are useful as raw materials for manufacturing high molecular weight substances, i.e., polymeric substances, such as fibers, synthetic resins, and the like, and in particular, for manufacturing high molecular weight substances with high heat resistance.

2. Description of the Prior Art

The manufacture of alcohols by the catalytic hydrocracking of the corresponding carboxylic acid ester is commonly known. For example, in "Organic Reaction", Vol. VIII, pages 1-27, John Wiley & Sons, New York (1954), the reaction conditions for the production of alcohols and yields obtainable thereby when using Adkins-type catalyst containing Cu-Cr oxides as the main components are summarized by H. Adkins. However, the catalytic hydrocracking using an Adkins-type catalyst under high temperature and high pressure was originally developed for the purpose of producing aliphatic alcohols from corresponding aliphatic carboxylic acid esters. When this process is used without modification for catalytic hydrocracking of aromatic carboxylic acid ester, significant amounts of aromatic alcohols are excessively reduced to produce aromatic hydrocarbons.

British Patent No. 1,254,927 discloses a process intended to suppress such side reactions by using copper oxide containing one or more of the oxides or carbonates, or both, of metals selected from the group consisting of magnesium, calcium, strontium, and barium as the catalyst. Also, Japanese Patent Publication No. Sho 47(1972)-35419 discloses an aromatic alcohol production process of liquid phase hydrogenation in the presence of a mixed catalyst of copper and (1) strontium, or (2) zinc and chromium, or (3) nickel and magnesium. Further, Japanese Patent Publication No. Sho 49(1974)-31435 discloses a process for preparing an aromatic alcohol by catalytic hydrocracking of corresponding aromatic carboxylic acid ester by using a catalyst comprising copper oxide containing alumina, magnesia, and chromium oxide, or, a catalyst comprising copper oxide containing magnesia, chromium oxide, and iron oxide.

Although these catalysts mentioned above have been proposed for the process for catalytic hydrocracking of aromatic polycarboxylic acid ester, because the conversion rate of the aromatic polycarboxylic acid esters is low and the yield of the aromatic polyhydric alcohols is low, too, development of an improved process is desired.

Specifically, the conversion rate of esters in the British Patent No. 1,254,927 is about 50 to 80% and selectivity to alcohol is 40 to 70%, so that the yield of polyhydric alcohols obtained by this process is at best 60%. Also, in Japanese Patent Publication No. Sho 47(1972)-35419, the selectivity is slightly improved, but the conversion rate is 40% or less. The catalyst used in Japanese Patent Publication No. Sho 49(1974)-31435 has a high selectivity of about 80% or greater but the conversion rate is 70% or less.

Thus, processes heretofore proposed can only provide a low conversion rate of aromatic polycarboxylic acid esters. The yield of aromatic polyhydric alcohols obtained by these processes has been unsatisfactory, too. These drawbacks further necessitate several process steps for separation and purification of aromatic polyhydric alcohols from the reaction products.

SUMMARY OF THE INVENTION

This invention can provide a route to overcome the deficiencies discussed above relative to the prior art processes.

We have conducted extensive studies with the objective of increasing the yield of aromatic polyhydric alcohols. As a result of experiments using various kinds of aromatic polycarboxylic acid esters having different alkyl groups, i.e., alcohol residues, it has been discovered that an extremely high conversion rate of raw material ester and an extremely high yield of an aromatic polyhydric alcohol can be obtained when an aromatic polycarboxylic acid alkyl ester, wherein the alkyl group is a normal or branched chain alkyl group having at least 6 carbon atoms, is used as raw material. We have further found that the reaction mentioned above can effectively be proceeded to give the best result when methanol is used as the reaction solvent. Still further, we have also discovered that to conduct the reaction mentioned above, copper-chromium oxides catalyst containing barium oxide and/or manganese oxides are the best catalysts. Such findings have led to the completion of the present invention.

Accordingly, the primary object of the present invention is to provide a process for preparing an aromatic polyhydric alcohol in an extremely high selectivity and an extremely high yield by a catalytic hydrocracking of the corresponding aromatic polycarboxylic acid ester.

The second object of the present invention is to provide a simple but an effective process for preparing an aromatic polyhydric alcohol suited for industrial applications.

Other object of the present invention will be apparent to the persons in the art from the detailed descriptions and the examples given hereunder.

Thus, the gist of the present invention resides in a process for preparing an aromatic polyhydric alcohol by the catalytic hydrocracking of an aromatic carboxylic acid ester, characterized in that an ester represented by the general formula $Ar(COOR)_{m'}(CH_2OH)_{n'}$ (wherein Ar means an aromatic group, R is independently selected from normal and branched alkyl groups having at least 6 carbon atoms, and $m'$ is an integer of at least 1, $n'$ is zero or a positive integer and $m'+n'$ satisfies the relationship $m'+n' \geq 2$) is used as raw material.

DETAILED DESCRIPTION OF THE INVENTION

The alkyl groups, i.e., alcohol residues, in the aromatic polycarboxylic acid ester used in the present invention may be the same or they may be different. It is also possible to use a mixture of the esters derived from many types of alcohols as the raw material ester. The alcohol can be a primary, secondary, or tertiary saturated aliphatic monohydric alcohol having 6 or more carbon atoms.

As examples of the alcohols which are used for the production of raw material esters to be used in the process of the present invention, 2,3-dimethyl-2-butanol, 3,3-dimethyl-1-butanol, 3,3-dimethyl-2-butanol, 2-ethyl-1-butanol, 1-hexanol, 2-hexanol, 3-hexanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 2,2-dimethyl-3-pentanol, 2,3-dimethyl-3-pentanol, 2,4-dimethyl-3-pentanol, 2,4-dimethyl-2-pentanol, 4,4-dimethyl-2-pentanol, 3-ethyl-3-pentanol, 1-heptanol, 2-heptanol, 3-heptanol, 2-methyl-2-hexanol, 2-methyl-3-hexanol, 5-methyl-2-hexanol, 4-methyl-3-heptanol, 6-methyl-2-heptanol, 1-octanol, 2-octanol, 3-octanol, 2-propyl-1-pentanol, 2,4,4-trimethyl-1-pentanol, 2-ethylhexanol, 2,6-dimethyl-4-heptanol, 1-nonanol, 2-nonanol, 3,5,5-trimethyl-1-hexanol, monomethyloctanol, 2,2-dimethyl-1-heptanol, 1-decanol, 2-decanol, 4-decanol, 1-undecanol, 1-dodecanol, 1-tridecanol can be cited.

As stated above, though any one of primary, secondary, or tertiary alcohols can be used to prepare raw material esters to be used in the process of the present invention, it is generally preferable to use primary alcohols as they can easily be converted into esters.

There are a number of processes for manufacturing the ester of an aromatic polycarboxylic acid which is to be subjected to catalytic hydrocracking in the process of the present invention, but usually it is manufactured by the esterification reaction of an aromatic polycarboxylic acid or an aromatic polycarboxylic acid anhydride and an alcohol.

The aromatic polycarboxylic acid used in the esterification reaction with the alcohol does not necessarily be limited to an aromatic polycarboxylic acid, but may include compounds which are partly esterified and hydrocracked compounds of the esters mentioned just above. Such a compound is represented by the general formula $Ar(COOH)_l(COOR)_m(CH_2OH)_n$ (wherein Ar is an aromatic group such as a monocyclic aromatic ring, a bi- or tri-cyclic condensed aromatic ring or a biphenyl ring (for example, a benzene ring, a naphthalene ring, an anthracene ring, a phenanthrene ring, or a biphenyl ring); R is the above-mentioned alkyl group, and l is an integer of at least 1, and m and n are zero or positive integers which satisfy the relationship $l+m+n \geq 2$).

As examples of aromatic polycarboxylic acids which are used for the production of the esters to be used in the process of the present invention, phthalic acid, isophthalic acid, terephthalic acid, 1,2,3-benzenetricarboxylic acid, 1,2,4-benzenetricarboxylic acid, 1,3,5-benzenetricarboxylic acid, 1,2,3,4-benzenetetracarboxylic acid, 1,2,3,5-benzenetetracarboxylic acid, 1,2,4,5-benzenetetracarboxylic acid, benzenepentacarboxylic acid, benzenehexacarboxylic acid, 2,3-naphthalenedicarboxylic acid, 2,6-naphthalenedicarboxylic acid, 4,5-phenanthrenedicarboxylic acid, 2,2'-biphenyldicarboxylic acid, 4-4'-biphenyldicarboxylic acid can be cited.

The esterification reaction of the above-mentioned aromatic polycarboxylic acid and alcohol can proceed either with or without the presence of a catalyst to produce the aromatic polycarboxylic acid ester which is the raw material for the process of the present invention. Commonly known catalysts may be used in the esterification reaction. Examples are acid catalysts such as p-toluene sulfonic acid, methane sulfonic acid, ethane sulfonic acid, ion exchange resins, heteropoly acid, sulfuric acid, phosphoric acid, and the like; suspensions of insoluble catalysts such as tin oxide, zinc oxide, antimony oxide, titanium oxide, silica-alumina compounded oxides, and the like; titanium compounds, such as tetraisopropyl titanate, tetrabutyl titanate, tetra (2-ethylhexyl) titanate, polymers of these compounds and the like; and tin compounds such as tin oxalate, tin tetrabutyrate, tin tetraacetate, and the like. Generally, however, in consideration of the effect on the catalyst used in the hydrocracking of the present invention, it is desirable to use a catalyst which contains no halogens or sulfur.

The descriptions above concern with the preparation of ester which is usable in the process of the present invention as starting raw material. As stated hereinbefore, the process of the present invention can be conducted well if the starting raw material satisfies the general formula $Ar(COOR)_{m'}(CH_2OH)_{n'}$ defined above and the process for the preparation thereof is not necessarily limited to the process described above. Now, the operation of catalytic hydrocracking of the present invention will be described in detail.

Commonly known catalysts are used as a catalyst for the hydrocracking in the process of the present invention. Examples of the catalysts are catalysts containing iron, nickel, cobalt, copper, copper chromite, platinum, or the like as the main components. However, to obtain higher yields, it is desirable to use a copper chromite-type catalyst containing barium or manganese. The catalyst mentioned above per se can be used, but the catalyst may also contain a small amount, e.g. less than several %, of lubricant such as graphite and a small amount, e.g. less than about 10%, of binder such as alumina. It is not preferable to use large amounts of lubricant and/or binder, because existence of large amounts of lubricant and binder decreases the content of the active catalyst. These catalysts are used in the reaction after first being subjected to a suitable activation treatment, for example, a reduction treatment. The catalyst may be used in any suitable form, such as powder form, tablet form, or any other forms, whichever is the most appropriate.

The hydrocracking reaction can be carried out in batchwise or continuously. It is desirable to carry out this reaction continuously by the use of trickle bed reactor, i.e., one kind of fixed bed flow-type reactors in which the reactant trickles to contact with a fixed catalyst bed or beds. The amount of catalyst used is about 0.1 to 100 times by volume of the amount of the aromatic polycarboxylic acid ester fed per one hour. If the value is expressed in the term of liquid houly space velocity (LHSV), the value corresponds to 0.01-10 $hr^{-1}$.

When conducting the catalytic hydrocracking reaction in batchwise, the reaction time may be within a range of 5 min to 10 hr. The reaction is preferably conducted under agitation by the use of an autoclave with shaking apparatus or agitator.

The operating conditions for the hydrocracking reaction generally vary depending on the kind of the aromatic polycarboxylic acid ester used as the raw material. The operating conditions generally applied are as follows.

The temperature range is 60° to 200° C. with the most desirable range being 60° to 150° C. Side reactions tend to partially occur if the temperature exceeds 200° C.; while below 60° C., the reaction rate is too low so that the reaction is not feasible practically. Generally, the higher the partial pressure of the hydrogen when the reaction takes place, the easier it is for the reaction to proceed, and in practice the partial pressure of the hydrogen must be at least 100 Kg/cm$^2$G. A hydrogen partial pressure in the 130 to 400 Kg/cm$^2$G is particularly desirable.

The hydrogen gas used in this reaction does not necessarily have to be of high purity. It may contain other components such as $N_2$ and $CH_4$, or impurities which do not have any detrimental effect on hydrocracking reaction. The amount of hydrogen to be supplied to the hydrocracking reaction is not necessarily limited, but the appropriate amount of hydrogen to be supplied is 2 to 4 moles per one equivalent of the ester group contained in the raw material, i.e., aromatic polycarboxylic acid ester.

This reaction can be carried out without the use of a solvent. However, it is generally more desirable to use a solvent. A material which acts to the detriment of the reaction must not be contained in the solvent. Alcohols and ethers are desirable solvents. A monohydric alcohol with a low number of carbon atoms, especially methanol, will provide a high conversion rate and a high yield.

The aromatic polyhydric alcohol product is usually separated by means of distillation from the monohydric alcohol which is also present in the liquid product of the hydrocracking reaction. The separated monohydric alcohol is recycled for use in the esterification reaction with the aromatic polycarboxylic acid. Partially hydrogenated product or products contained in the liquid product of the hydrocracking reaction may be recycled to the hydrocracking step.

As materially shown in the following examples, the process of the present invention can provide an extremely high conversion rate of the raw material aromatic polycarboxylic acid ester, and, in addition, the selectivity to the aromatic polyhydric alcohol is also high. Accordingly, it is possible to maintain the concentration of aromatic polyhydric alcohol in the liquid reaction product in an extremely high level. For this reason, the separation and purification processes for the aromatic polyhydric alcohol in the resulting reaction liquid can be simplified significantly. The present invention, therefore, has high merit as an industrial process.

DESCRIPTION OF THE PREFERRED EMBODIMENT

The present invention will now be explained in detail with reference to the following examples. However, these examples are by way of illustration only and are in no way restrictive of the present invention.

Example 1

Commercially available barium-containing copper chromite catalyst (Cu-1184-T, manufactured by Harshaw Co.; CuO 43%, $Cr_2O_3$ 45%, BaO 9%) was used as the catalyst. The size of the catalyst used was approximately trigonal prism type which was obtained by cutting commercially available pelletized form catalyst with 3 mm diameter and 3 mm height into 8 pieces. The catalyst (32.5 g) was placed in a tubular reactor with 10 mm diameter and 500 mm length. The volume of catalyst was about 25 ml. The catalyst was activated by conventional hydrogen reduction treatment (Firstly, the catalyst was subjected to a hydrogen reduction treatment in a flow of nitrogen gas containing 1 to 5% hydrogen at a temperature of 170° C. or lower, then the material was subjected to a further reduction treatment for one hour at 150° C. in a 50/50 (v/v) $H_2/N_2$ atmosphere.). Thereafter, the catalyst was served to the hydrocracking reaction of the present invention. Hydrogen gas was passed to the tubular reactor in a flow rate of 5 liters per hour measured at the outlet of the reactor under a reaction temperature of 100° C. and reaction pressure of 200 Kg/cm$^2$G. A methanol solution containing 15 wt of di(2-ethylhexyl) isophthalate was fed as a raw material at a rate of 41.0 g/hr (LHSV=2.0 hr$^{-1}$) from the upper part of the tubular reactor together with hydrogen. Incidentally, basis for calculation of LHSV shown above is the volume of methanol solution charged per hour per volume of the catalyst used, hereinafter the same.

The results of analysis by gas chromatography of the liquid reaction product showed that the conversion rate of the di(2-ethylhexyl) isophthalate was 98.9%, while the selectivities to the objective m-xylylene glycol, the by-product m-methylbenzyl alcohol and the intermediate 2-ethylhexyl m-hydroxymethylbenzoate were 84.0%, 13.2%, and 1.43%, respectively.

Example 2

Into a 100 ml autoclave with a shaking apparatus, 4.4 g of di(2-ethylhexyl) isophthalate, 40 ml of methanol, and a commercial barium-containing copper chromite catalyst (4.0 g of Cu-1184-T catalyst, manufactured by Harshaw Co. and pulverized before use) which was subjected to a reducing treatment with hydrogen in the same way as in Example 1 were added. After the pressure was repeatedly raised and lowered by hydrogen to expel all the air, the autoclave was filled with hydrogen to a pressure of 150 Kg/cm$^2$G at room temperature and the autoclave was sealed. Then, the reaction was carried out for one hour at 120° C. under shaking.

The results of analysis of the liquid reaction product were as follows. The conversion rate of the di(2-ethylhexyl) isophthalate was 95.6%, while the selectivities to the objective m-xylylene glycol, the by-product m-methylbenzyl alcohol and the intermediate 2-ethylhexyl m-hydroxymethylbenzoate were 82.3%, 11.5%, and 5.1%, respectively.

Example 3

The reaction of Example 2 was repeated exactly except that di(2-ethylhexyl) terephthalate was used instead of the di(2-ethylhexyl) isophthalate used in Example 2.

The results of analysis of the liquid reaction product were as follows. The conversion rate of the di(2-ethylhexyl) terephthalate was 98.1%, while the selectivities to the objective p-xylylene glycol, the by-product p-methylbenzyl alcohol and the intermediate 2-ethylhexyl p-hydroxymethylbenzoate were 84.7%, 3.5%, and 10.5%, respectively.

Example 4

The reaction was carried out exactly in the same way as in Example 2 except that 4 g of a commercial manganese-containing copper chromite catalyst (Cu-1924-T, manufactured by Harshaw Co.; CuO 46%, $Cr_2O_3$ 46%, $MnO_2$ 4%) was used as the catalyst and 5 g of di(2-ethylhexyl) 2,6-naphthalenedicarboxylate was used instead of the di(2-ethylhexyl) isophthalate.

The results of analysis of the liquid reaction product were as follows. The conversion rate of the di(2-ethylhexyl) 2,6-naphthalenedicarboxylate was 99.5%, while the selectivities to the objective 2,6-dihydroxymethylnaphthalane, the by-product 2-hydroxymethy-6-methylnaphthalene and the intermediate 2-ethylhexyl 2-hydroxymethy-6-naphthoate were 93.0%, 1.2%, and 5.8%, respectively.

Example 5

The reaction of Example 2 was repeated exactly except that ethanol was used instead of methanol as used in Example 2.

The results of analysis of the liquid reaction product by gas chromatography were as follows. The conversion rate of the di(2-ethylhexyl) isophthalate was 89.2%, while the selectivities to the objective m-xylylene glycol, the by-product m-methylbenzyl alcohol and the intermediate 2-ethylhexyl m-hydroxymethylbenzoate were 77.3%, 14.8%, and 7.9%, respectively.

Example 6

The reaction of Example 2 was repeated exactly except that a commercial copper chromite catalyst (Cu-0203-T, manufactured by Harshaw Co.; CuO 79%, $Cr_2O_3$ 17% ) was used as the catalyst.

The results of analysis of the liquid reaction product were as follows. The conversion rate of the di(2-ethylhexyl) isophthalate was 90.2%, while the selectivities to the objective m-xylylene glycol, the by-product m-methylbenzyl alcohol and the intermediate 2-ethylhexyl m-hydroxymethylbenzoate were 74.5%, 11.2%, and 11.5%, respectively.

Example 7

The reaction of Example 4 was repeated exactly except that 5 g of di(2,6-dimethyl-4-heptyl) isophthalate was used instead of di(2-ethylhexyl) 2,6-naphthalenedicarboxylate and the amount of methanol was changed to 30 ml.

The results of analysis of the liquid reaction product by gas chromatography were as follows. The conversion rate of the di(2,6-dimethyl-4-heptyl) isophthalate was 98.5%, while the selectivities to the objective m-xylylene glycol, the by-product m-methylbenzyl alcohol and the intermediate 2,6-dimethyl-4-heptyl m-hydroxymethylbenzoate were 86.1%, 2.3%, and 11.6%, respectively.

Example 8

The reaction of Example 3 was repeated exactly except that 4.4 g of di(n-octyl) terephthalate was used instead of di(2-ethylhexyl) terephthalate.

The results of analysis of the liquid reaction product by gas chromatography were as follows. The conversion rate of the di(n-octyl) terephthalate was 96.3%, while the selectivities to the objective p-xylylene glycol, the by-product p-methylbenzyl alcohol and the intermediate n-octyl p-hydroxymethylbenzoate were 84.0%, 3.8%, and 12.2%, respectively.

Example 9

This example is not within the scope of the present invention, and is given for comparative purpose only.

The reaction of Example 1 was repeated exactly except that a 10 wt % methanol solution of dimethyl isophthalate was used as a raw material, the reaction temperature was 125° C., and the LHSV was 1.3 $hr^{-1}$.

As a result, the conversion rate of the dimethyl isophthalate was 59.2%, while the selectivities to the objective m-xylylene glycol, the by-product m-methylbenzyl alcohol and the intermediate methyl m-hydroxymethylbenzoate were 45.7%, 38.3%, and 14.9%, respectively.

Example 10

This example is not within the scope of the present invention, and is given for comparative purpose only.

The reaction of Example 2 was repeated exactly except that 2.2 g of dimethyl isophthalate was used in place of the 4.4 g of di(2-ethylhexyl) isophthalate, the reaction temperature was 125° C., and reaction time was 1.5 hours.

As a result, the conversion rate of the dimethyl isophthalate was 75.8%, while the selectivities to the objective m-xylylene glycol, the by-product m-methylbenzyl alcohol and the intermediate methyl m-hydroxymethylbenzoate were 65.1%, 22.8%, and 12.1%, respectively.

Example 11

This example is not within the scope of the present invention, and is given for comparative purpose only.

The reaction of Example 2 was repeated exactly except that 3.2 g of dibutyl isophthalate was used in place of the 4.4 g of di(2-ethylhexyl) isophthalate, the reaction temperature was 125° C., and reaction time was 1.5 hours.

As a result, the conversion rate of the dibutyl isophthalate was 74.1%, while the selectivities to the objective m-xylylene glycol, the by-product m-methylbenzyl alcohol and the intermediate butyl m-hydroxymethylbenzoate were 67.3%, 20.9%, and 11.8%, respectively.

We claim:

1. In a process for preparing an aromatic polyhydric alcohol represented by the general formula $Ar(CH_2OH)_{m'+n'}$ by catalytic hydrocracking of an aromatic carboxylic acid ester in the presence of a copper-chromite-type catalyst at a temperature of 60°–200° C. and under a hydrogen partial pressure of 100–400 $Kg/cm^2G$, an improvement which comprises using an ester represented by the general formula $Ar(COOR)_{m'}(CH_2OH)_{n'}$ as raw material wherein:

Ar is selected from the group consisting of benzene ring, naphthalene ring, anthracene ring, phenanthrene ring and biphenyl ring, R is independently selected from normal and branched alkyl groups having 6–13 carbon atoms, m' is an integer of at least 1, n' is zero or a positive integer, and m'+n' satisfies the relationship m'+n'≧2.

2. The process of claim 1, wherein Ar means a benzene ring or a naphthalene ring.

3. The process of claim 1, wherein said catalyst is a copper-chromite catalyst containing barium oxide and/or manganese oxides.

4. The process of claim 1, wherein said temperature is 60°–150° C. and said pressure is 130–400 $Kg/cm^2G$.

5. The process of claim 1, wherein R is a primary alkyl group.

6. The process of claim 1, wherein said catalytic hydrocracking is carried out in the presence of a solvent.

7. The process of claim 6, wherein said solvent is selected from the group consisting of alcohols and ethers.

8. The process of claim 6, wherein said solvent is methanol.

9. The process of claim 1, wherein said catalytic hydrocracking is carried out in batches by using a reaction time of 5 min–10 hr.

10. The process of claim 1, wherein said catalytic hydrocracking is carried out continuously by using fixed bed flow-type reactor and under a raw material charge rate in the term of LHSV of 0.01–10 hr$^{-1}$.

11. The process of claim 10, wherein said reactor is trickle bed reactor.

12. The process of claim 4, wherein said R is an alkyl group having 8 or 9 carbon atoms, and said hydrocracking is carried out in the presence of a lower alcohol as the solvent.

13. The process of claim 12, wherein said R is a 2-ethylhexyl, 2,6-dimethyl-4-heptyl or n-octyl group, said catalyst is copper-chromite catalyst containing barium oxide and/or manganese oxides and said solvent is methanol.

14. The process of claim 13, wherein said catalytic hydrocracking is carried out continuously by using trickle bed reactor under a raw material charge rate in the term of LHSV of 0.01–10 hr$^{-1}$.

15. The process of claim 13, wherein said R is a 2-ethylhexyl group.

16. The process of claim 13, wherein said Ar is a benzene ring or a naphthalene ring.

* * * * *

UNITED STATES PATENT AND TRADEMARK OFFICE
CERTIFICATE OF CORRECTION

PATENT NO. : 4,990,690
DATED : February 5, 1991
INVENTOR(S) : Yuji Onda et al

It is certified that error appears in the above—identified patent and that said Letters Patent is hereby corrected as shown below:

On the Title Page, Please correct the inventorship of the third-named inventor by deleting the surname "Tunoda" and substituting therefor the correct name -- Tsunoda --.

Signed and Sealed this

Twenty-seventh Day of April, 1993

Attest:

MICHAEL K. KIRK

Attesting Officer        Acting Commissioner of Patents and Trademarks